(12) United States Patent
Kao

(10) Patent No.: US 9,989,465 B2
(45) Date of Patent: Jun. 5, 2018

(54) MULTI-CHANNEL FLUORESCENCE DETECTING SYSTEM AND METHOD OF USING THE SAME

(71) Applicant: TAIGEN BIOSCIENCE CORPORATION, Taipei (TW)

(72) Inventor: Hung-Jen Kao, Taipei (TW)

(73) Assignee: TAIGEN BIOSCIENCE CORPORATION, Taipei (TW)

( * ) Notice: Subject to any disclaimer, the term of this patent is extended or adjusted under 35 U.S.C. 154(b) by 0 days. days.

(21) Appl. No.: 15/598,236

(22) Filed: May 17, 2017

(65) Prior Publication Data

US 2017/0370842 A1 Dec. 28, 2017

(30) Foreign Application Priority Data

Jun. 24, 2016 (TW) .............................. 105120034 A

(51) Int. Cl.
| | |
|---|---|
| *F21V 9/16* | (2006.01) |
| *G01N 21/64* | (2006.01) |
| *C12Q 1/68* | (2018.01) |

(52) U.S. Cl.
CPC ......... *G01N 21/6428* (2013.01); *C12Q 1/686* (2013.01); *G01N 2021/6439* (2013.01)

(58) Field of Classification Search
CPC .................. G01N 2201/0627; G01J 2003/106
See application file for complete search history.

(56) References Cited

U.S. PATENT DOCUMENTS

2010/0032582 A1* 2/2010 Xia ........................... G01J 3/02
250/458.1
2012/0295268 A1* 11/2012 Furlan ................ G01N 21/6428
435/6.12

(Continued)

FOREIGN PATENT DOCUMENTS

| CN | 1494655 A | 5/2004 |
|---|---|---|
| CN | 201107270 Y | 8/2008 |
| CN | 104655318 A | 5/2015 |

OTHER PUBLICATIONS

"Fundamentals of Light-Emitting Diodes (LEDs)", Carl Zeiss Microscopy Online Campus p. 1-12, available at http://zeiss-campus.magnet.fsu.edu/print/lightsources/leds-print.html.*

*Primary Examiner* — Kenneth J Malkowski
(74) *Attorney, Agent, or Firm* — Cheng-Ju Chiang

(57) ABSTRACT

The present invention provides a multi-channel fluorescence detecting system for detecting a plurality of fluorescence labeled analytes. The multi-channel fluorescence detecting system comprises a light source, a light filter device, a dual branch light guide tube, and a detector. The light source comprises a plurality of sub light sources for respectively providing an excitation light. The plurality of sub light sources are a plurality of single color Light emitting diodes (LEDs) which can be selectively turned on or off. The light source generates a plurality of lights with full width at half maximum (FWHM) wavelengths formed in a non-overlap manner. With the disposition of the plurality of sub light sources, the accuracy for detecting the specific analytes is raised, the light flux with a specific wavelength band is effectively raised (without raising the light flux of the full wavelength band), the structure is simplified, and the manufacturing cost is decreased.

10 Claims, 6 Drawing Sheets

(56) References Cited

U.S. PATENT DOCUMENTS

2013/0102481 A1\* 4/2013 McCollum ......... G01N 21/6428
506/9
2014/0045250 A1 2/2014 Kreifels et al.
2014/0191138 A1\* 7/2014 Atzler ................... G01N 21/31
250/458.1

\* cited by examiner

MULTI-CHANNEL FLUORESCENCE DETECTING SYSTEM AND METHOD OF USING THE SAME

FIELD OF THE INVENTION

The present invention relates to a multi-channel fluorescence detecting system and a method of using the same, and in particular, which is related to the field of biochemistry, for detecting specimens, which reacts to certain wavelength bands.

BACKGROUND OF THE INVENTION

In the field of biochemistry, it is commonly known to employ the fluorescence detecting technique for the detection of samples. Because the fluorescence detecting technique does not need to contact with to-be-test samples, non-destructive quantitative or qualitative measurements of the to-be-test samples can be done by operators without exposing to highly contagious environment. This leads to wider usage of the technique.

Fluorescence detection is to utilize certain components of an analyte being bound to a specific fluorescent dye which has a photoluminescence characteristic for a specific wavelength of light spectrum. Consequently, by illuminating the analysis of samples under a constant-intensity incident light, emission spectrums of the samples can be measured as analyzing types or concentrations of the samples. Common fluorescent dyes comprises FAM in blue-light band, HEX in green-light band, TAMRA in yellow-light band, ROX in orange-light band, CY5 in red light band, and Red670 in deep red light band.

Polymerase chain reaction (PCR) is a molecular biology technique, which can be used to expand specific DNA fragments with appropriate agents and thermal cycle equipment. And after each thermal cycle, when the reactants are detected by a fluorescence detecting system, a method for qualitative analysis or quantitative analysis for the total amount of specific products in the reactants is a real-time polymerase chain reaction (Real-time PCR).

In the field of biochemistry, multi-channel fluorescence detection typically employs real-time/quantitative polymerase chain reaction (real-time PCR or QPCR) methods. Furthermore, due to the diversity of to-be-test samples and reagents, the light source of the equipment generally comprises one or more wavelength bands of ultraviolet, visible or infrared.

Referring to FIG. 1, a schematic diagram of a fluorescence detecting system 10 of a conventional art is shown. The fluorescence detecting system 10 includes a light source 11, an excitation-light guide tube 12, a fluorescence labeled analyte 13, an emission-light guide tube 14, an emission-light filter 15, and a detector 16. The operating flow is as follows. The light source 11 emits an excitation light 17; next, the excitation light 17 enters the excitation-light guide tube 12; next, the excitation light 17 illuminates the fluorescence labeled analyte 13 to generate an emission light 18; next, the emission light 18 enters the emission-light guide tube 14; next, the emission light 18 enters the detector 16 through the emission-light filter 15; and finally, the detector 16 determines a type of the emission light 18. In general, in the present field, the excitation light 17 is a light that is used to illuminate the fluorescence labeled analyte 13, the emission light 18 is a light that has been reflected from the fluorescence labeled analyte 13. In general, the excitation-light guide tube 12 and the emission-light guide tube 14 are two paths independent from each other. This would increase the difficulty in assembly of the fluorescence detecting system 10.

In order to speed up and simplify the fluorescence detecting process, the light source 11 is capable of providing a variety of wavelength bands, and the emission-light filter 15 is a multiband emission filter.

In general, the conventional fluorescence detecting system employs a white light as a light source for rapid detection, since the fluorescence labeled analyte 13 may generates photoluminescence for a variety of wavelength bands. When the excitation light 17 illuminates the fluorescence labeled analyte 13 and further generates an emission light 18 having a plurality of wavelength bands is correspondingly generated; in other word, the emission light 18 comprises a variety of wavelength bands, correspondingly. Next, the emission light 18 is filtered by the emission-light filter 15, to produce alight with different wavelength bands. Thus, when the fluorescence labeled analyte 13 reacts for the light with different wavelength bands, it is possible to perform the detection, simultaneously, whereby the consumed time is reduced.

Although the conventional art can simultaneously detect a variety of wavelength bands, there are several existing problems therein. 1. When the light is white light, excessive emission light is generated therefrom; 2. Since when the emission light 18 passes through the emission-light filter 15, some wavelength bands, which do not need to be filtered, might be filtered out by the emission-light filter 15, thereby affecting the accuracy of the follow-up detection; 3. The emission-light filter 15 is made with employment of multilayer filters on the same glass piece by a special way, so that its production process and production cost get higher; 4. Although white light can be employed to emit light with a variety of wavelength bands at the same time, it may cause the emission light 18 generating other lights with unnecessary wavelength bands. The results in a miscarriage of justice.

Referring to FIG. 2, a schematic diagram of a fluorescence detecting system 20 of another conventional art is shown. A difference of the fluorescence detecting system 20 from the fluorescence detecting system 10 is addition of an excitation-light filter 19 into before the excitation light 17 is illuminated onto the fluorescence labeled analyte 13. More specifically, the excitation-light filter 19 is arranged between the light source 11 and the excitation-light guide tube 12 in the another conventional art.

Although the fluorescence detecting system 20 improves the efficiency of the fluorescence detection system 10 by providing the excitation-light filter 19. However, since when the emission light 18 passes through the emission-light filter 15, the emission light 18 may be filtered in those wavelength bands which does not need to be filtered, thus affecting the accuracy of subsequent detection, such that other technical problems are still un-solved.

Furthermore, in another conventional art, a fluorescence detecting system 20 employs a plurality of sensors to rapidly perform a detection operation, but a plurality of sensors still brings the system cost increased and assembly difficult.

In summary, the conventional arts almost employ a light source (i.e., a white light) which is capable of generating multi-wavelength bands in order to increase detection efficiency but reducing the accuracy of detection for a single wavelength band.

Such as Thermo Fisher QuantStudio 12K Flex and Roche LightCycler 480 and other products, are used in the visible band of white LED fluorescence detecting system as light sources, of the white LED light, these kinds of white LED has become the mainstream of visible light source for the emitting wavelength of the white LED can cover the visible light wavelength band, sufficient brightness, cheap, light weight, small size, low power consumption, and vibration resistance.

A generation mechanism of emitting white light by the white light emitting diode is to apply a voltage on a GaN PN diode chip which is capable of emitting blue light, and to arrange a fluorescence substance, which can be excited by the blue light, in front of the blue light chip, whereby after excitated, the fluorescence substance correspondingly generates fluorescence light, such as in green, yellow, red, in order to accomplish the generation of white light. The spectral distribution of the white light emitting diodes mainly depend on a superposition among emission wavelengths of the blue light LED chip and the various fluorescent light generated by the various fluorescent substances. When the white LED power is activated, a fixed spectral distribution of visible light can be given; namely, as long as light intensity of each wavelength in the spectrum is fixed, their wavelengths and color brightness are unable to be controlled. Therefore, in real-time PCR application, if intending to strengthen the intensity of a certain color excitation light, we can only apply higher voltage on the blue LED chip, so that the overall white LED light-emitting bands become brighten at the same time, and then the light need to pass through the filter so as to derive a higher-brightness monochromatic light. This causes the overall energy consumption efficiency of such a white LED light source lowered as well as easily causing unnecessary waste of light and electricity. When a greater current passes through the LED chip, more heat is generated therein, so that the conversion efficiency from electric energy to light is low, and also aging of the light source is accelerated. In addition, for a long time, there is no fluorescent substance suitably cooperated with the white LED in the deep red band. This leads to a puzzle of applying the white LED in the red band.

To complement the shortcomings of a single white LED, some real-time PCR detector manufacturers, such as TOptical Thermocycler in Germany, Biometra, in the light source of the fluorescence detection area, besides using the white LED, respectively adds a red LED and a blue LED in the optical paths so as to compensate the issue of insufficient light-emitting band. However, this causes that the optical design becomes complicated, and the instability of the instrument is raised.

In another conventional art, a fluorescence detecting system employs four sensors to constitute a four-channel real-time PCR detector which allows scanning four fluoroscopic channels for one scan process, thereby reducing detection times. However, such a design of synchronous detection does not only increase the cost of optical sensors and optical paths, but also causes that the overall sensing area becomes large and complex.

As mentioned above, a plurality of LEDs are employed so as to compose a white light in the conventional art. However, the conventional fluorescence detecting system has to turn on all of the plurality of LEDs, in order to detect all the fluorescent labels at the same time; otherwise, the purpose of synchronous detection is unable to achieve.

Since most of the detections are done for specific objects, it is technical problems, which are urgent to be solved, of how to effectively increase the accuracy of detection of a specific wavelength band, effectively increase the luminous flux of a specific wavelength band (without increasing the full wavelength of the flux under the premise), and simplify the structure of the fluorescence detecting system and reduce production costs.

Hence, it is essential to provide a multi-channel fluorescence detecting system and a method of using the same to solve the above technical problems.

SUMMARY OF THE INVENTION

In order to solve the aforementioned technical problems of the conventional art, an objective of the present invention is to provide a multi-channel fluorescence detecting system, for detecting the plurality of fluorescence labeled analytes. The present invention solves the conventional technical problems, by using a light source which can generate a plurality of lights with Full width at half maximum (FWHM) wavelengths formed in a non-overlap manner, to make the accuracy of detection of specific analytes increased, the luminous flux of specific wavelength bands (without increasing the full wavelength of the flux under the premise) increased, the structure of the fluorescence detecting system simplified and production costs reduced.

In order to achieve the object, the present invention provides a multi-channel fluorescence detecting system, for detecting a plurality of fluorescence labeled analytes, which comprises a light source, a light filter device, a dual branch light guide tube and a detector.

The light source comprises a plurality of sub light sources for respectively providing an excitation light. The light filter device comprises at least one light filter set. Each of the at least one light filter set comprises an excitation-light filter and an emission-light filter. The excitation-light filter is used to receive the excitation light. The dual branch light guide tube comprises an emission-light guide tube and an excitation-light guide tube. The excitation-light guide tube is used to receive the excitation light which passes through the excitation-light filter. The emission-light guide tube is used to receive the emission light which is generated, by the excitation light illuminating the plurality of fluorescence labeled analytes, with corresponding to the excitation light. The detector is used to receive the emission light passing through the emission-light guide tube and the emission-light filter, for confirming types of the emission light.

In a preferred embodiment, the emission-light guide tube and the excitation-light guide tube are arranged, concentrically.

In a preferred embodiment, the dual branch light guide tube further comprises a scanning head for making the excitation light to illuminate the plurality of fluorescence labeled analytes and for receiving the emission light.

In a preferred embodiment, the multi-channel fluorescence detecting system further comprises a controller used for controlling relative movements among the light source, the light filter device, the dual branch light guide tube and the detector.

In a preferred embodiment, the light filter device further comprises a controlling device, which is used to cooperate with the excitation light and the emission light, for rotating the at least one light filter set.

In a preferred embodiment, the plurality of sub light sources are a plurality of single color light emitting diodes (LEDs) which can be selectively turned on or off.

In a preferred embodiment, the light source is used to generate a plurality of lights with FWHM wavelengths formed in a non-overlap manner.

In order to achieve the object, the present invention provides a multi-channel fluorescence detecting method for detecting a plurality of fluorescence labeled analytes. The multi-channel fluorescence detecting method comprises the following steps that: first, an excitation light is provided by each of a plurality of sub light sources of a light source; next, the excitation light enters an excitation-light guide tube of a dual branch light guide tube after passing through an excitation-light filter of at least one light filter set of a light filter device; next, an emission light is generated by illuminating the plurality of fluorescence labeled analytes with the excitation light from a scanning head of the dual branch light guide tube; next, the emission light from the scanning head enters an emission-light guide tube of the dual branch light guide tube; next, the emission light from the emission-light guide tube enters an emission-light filter of the at least one light filter set of the light filter device; next, the emission light enters a detector for confirming types of the emission light.

In a preferred embodiment, the method further comprises a step of: using a controller to control relative movements among the light source, the light filter device, the dual branch light guide tube and the detector, according to the types of the plurality of fluorescence labeled analytes.

In a preferred embodiment, the dual branch light guide tube further comprises a scanning head for making the excitation light to illuminate the plurality of fluorescence labeled analytes and for receiving the emission light.

In a preferred embodiment, the light filter device further comprises a controlling device used to cooperate with the excitation light and the emission light, for rotating the at least one light filter set.

In a preferred embodiment, the plurality of sub light sources are a plurality of single color light emitting diodes (LEDs) which can be selectively turned on or off.

In a preferred embodiment, the light source generates a plurality of lights with FWHM wavelengths formed in a non-overlap manner.

Compared with the conventional art, the present invention solves the conventional technical problems, by using a light source which can generate a plurality of lights with FWHM wavelengths formed in a non-overlap manner, to make the accuracy of detection of specific analytes increased, the luminous flux of specific wavelength bands (without increasing the full wavelength of the flux under the premise) increased, the structure of the fluorescence detecting system simplified and production costs reduced.

DESCRIPTION OF THE DRAWINGS

The technical solution and the beneficial effects of the present invention are best understood from the following detailed description with reference to the accompanying figures and embodiments.

DETAILED DESCRIPTION OF THE PREFERRED EMBODIMENTS

The following description of the embodiments is given by way of illustration with reference to the specific embodiments in which the invention may be practiced. The terms such as "up", "down", "front", "back", "left", "right", "inside", "outside", "side", etc., The direction of the diagram. Accordingly, the use of a directional term is used to describe and to understand the present invention and is not intended to limit the invention.

Figure 1:
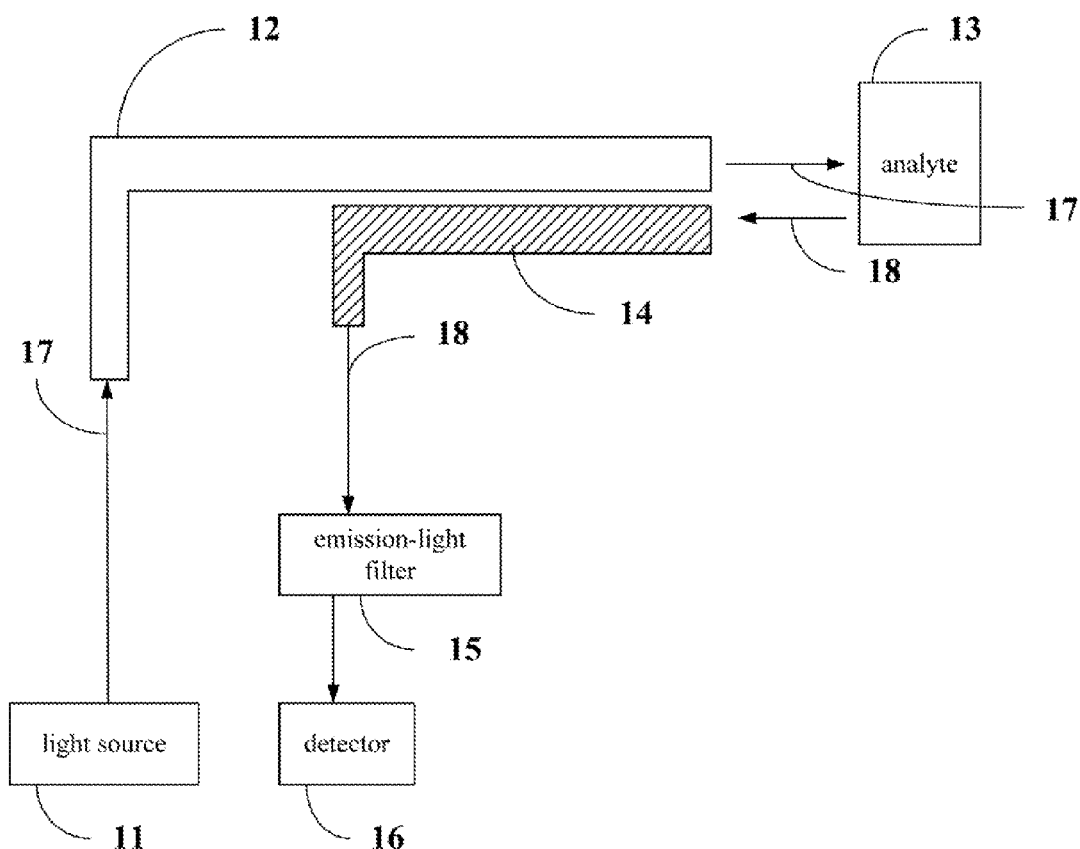
FIG. 1 is a schematic diagram of a conventional fluorescence detecting system.
Figure 2:
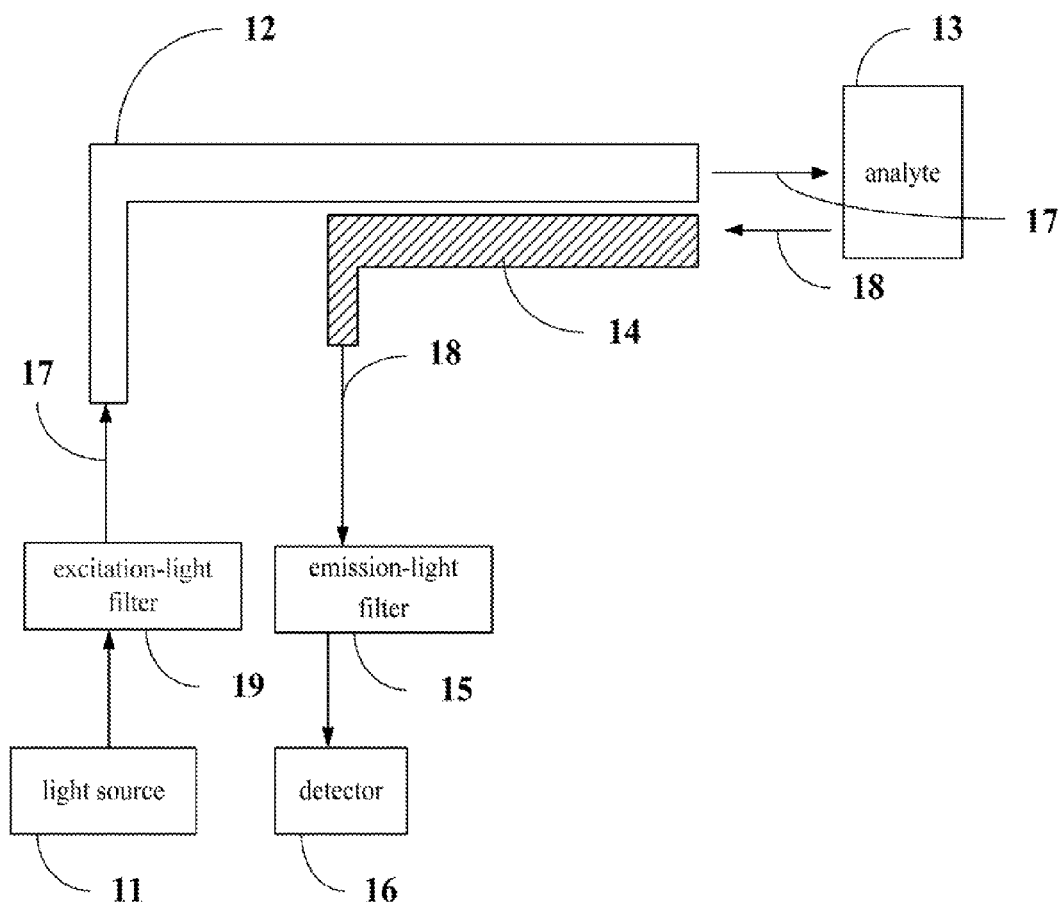
FIG. 2 is a schematic diagram of another conventional fluorescence detecting system.
Figure 3:
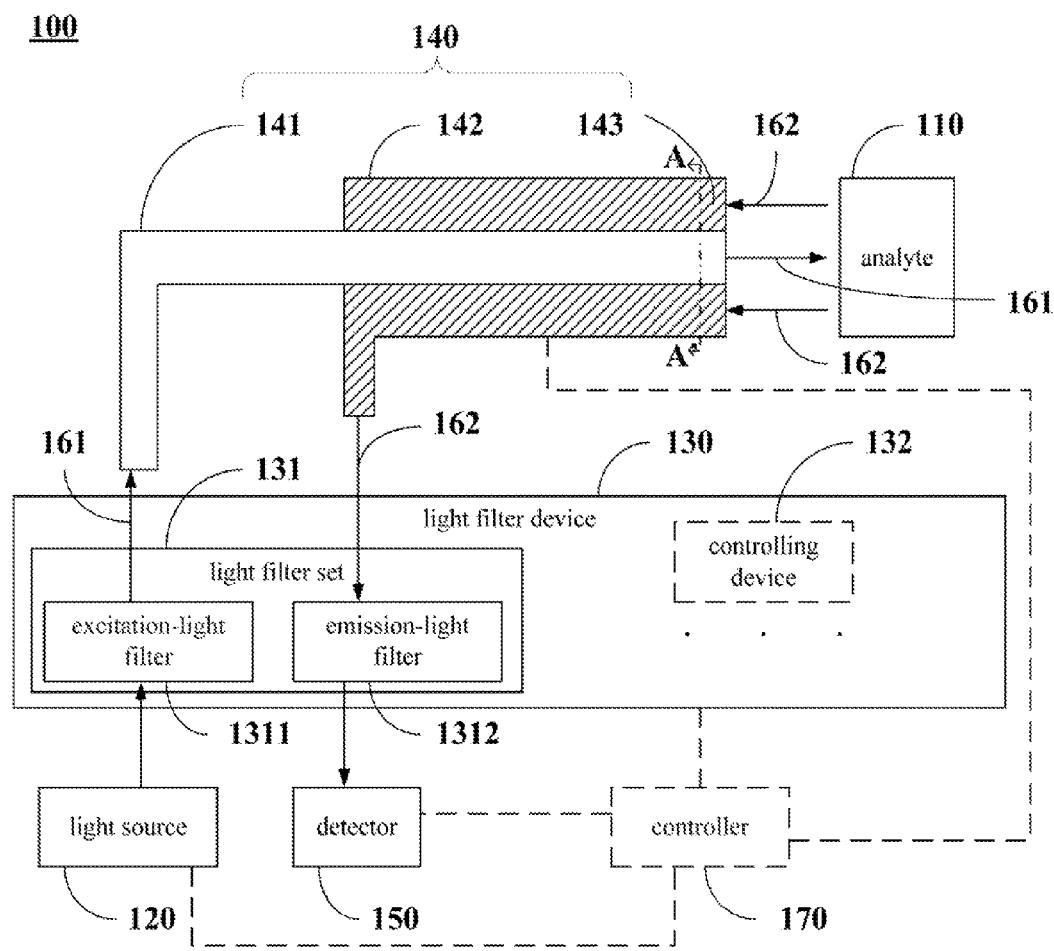
FIG. 3 is a schematic diagram of a fluorescence detecting system according to the present invention.
Figure 4:
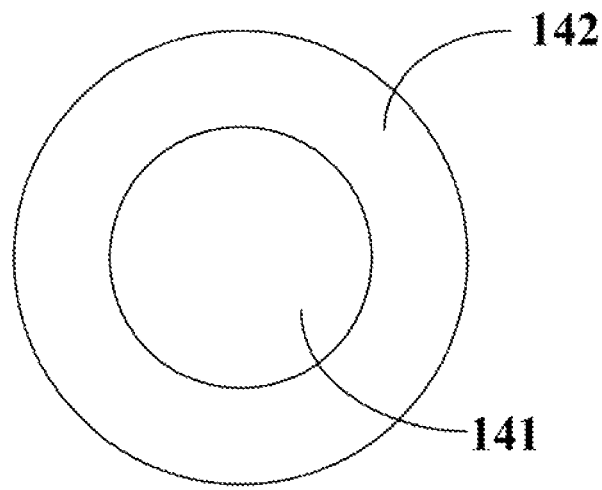
FIG. 4 is a cross-sectional diagram by a cutting line A-A' of FIG. 3.

Please refer to FIGS. 3-4. FIG. 3 is a schematic diagram of a fluorescence detecting system 100 according to the present invention, and FIG. 4 is a cross-sectional diagram by the cutting line A-A' in FIG. 3. The multi-channel fluorescence detecting system 100 for detecting a plurality of fluorescence labeled analytes 110, comprises a light source 120, a light filter device 130, a dual branch light guide tube 140, a detector 150 and a controller 170. Please note that in the drawings, the controller 170 is connected with the light source 120, the light filter device 130, the dual branch light guide tube 140 and the detector 150 in dashed lines which indicates that the multi-channel fluorescence detecting system 100 can manually operate one or more among the light source 120, the light filter device 130, the dual branch light guide tube 140 and the detector 150, according to different requests. In the preferred embodiment, only one fluorescence labeled analyte 110 is shown as an exemplary; however, in practice of automatic operation, the multi-channel fluorescence detecting system 100 can be used for detecting the plurality of fluorescence labeled analytes 110.

The light source 120 comprises a plurality of sub light sources for respectively providing an excitation light 161. The light filter device 130 comprises at least one light filter set 131 and a controlling device 132. Each of the at least one light filter set 131 comprises an excitation-light filter 1311 and an emission-light filter 1312. The controlling device 132 is used to cooperate with the excitation light 161 and the emission light 162, for rotating the at least one light filter set 131. Please note that the controlling device 132 is also represented by dashed lines to indicate that the multi-channel fluorescence detecting system 100 can manually rotate the at least one light filter set 131, according to different requests.

The excitation-light filter 1311 is used to receive the excitation light 161. The dual branch light guide tube 140 comprises an emission-light guide tube 142, an excitation-light guide tube 141 and a scanning head 143. The excitation-light guide tube 141 is used to receive the excitation light 161 passing through the excitation-light filter 1311. The emission-light guide tube 142 is used to receive the emission light 162 which is generated, by the excitation light 161 illuminating the plurality of fluorescence labeled analytes 110, with corresponding to the excitation light 161. The detector 150 is used to receive the emission light 162 passing through the emission-light guide tube 142 and the emission-light filter 1312, for confirming types of the emission light 162. Preferably, the emission-light guide tube 141 and the excitation-light guide tube 142 are arranged, concentrically. However, it is possible to design with different shapes on different demands, and without any limitation hereto.

The controller 170 is used for controlling relative movements among the light source 120, the light filter device 130, the dual branch light guide tube 140 and the detector 150. For example, when it is determined whether the fluorescence labeled analyte 110 reacts against a light with a specific wavelength (such as Full width at half maximum (FWHM)

wavelength in 430-500 nanometers) or not, the controller 170 can control the light source 120 to only emit the excitation light 161 with a specific wavelength (as FWHM wavelength in 450-470 nanometers). The controller 170 can control the controlling device 132 to rotate to a suitable one of the at least one light filter set 131, the excitation-light filter 1311 of the suitable light filter set 131 only permits the light with the specific wavelength (as FWHM wavelength in 450-460 nanometers) to pass therethrough (wherein the wavelength of the excitation light 161 is changed to avoid generation of unnecessary emission light). The emission-light filter 1312 of the light filter set 131 only permits the light with a specific wavelength (as FWHM wavelength in 490-520 nanometers) to pass therethrough (wherein the wavelength allowed to pass through the emission-light filter 1312 can be changed on demands). The controller 170 can control the dual branch light guide tube 140 to scan each of the plurality of fluorescence labeled analytes 110. In detail, the light-excitation filter 1311 and the emission-light filter 1312 respectively permits a light with only one wavelength to pass therethrough, in order to lower the manufacturing cost and raise the accuracy.

Figure 5:
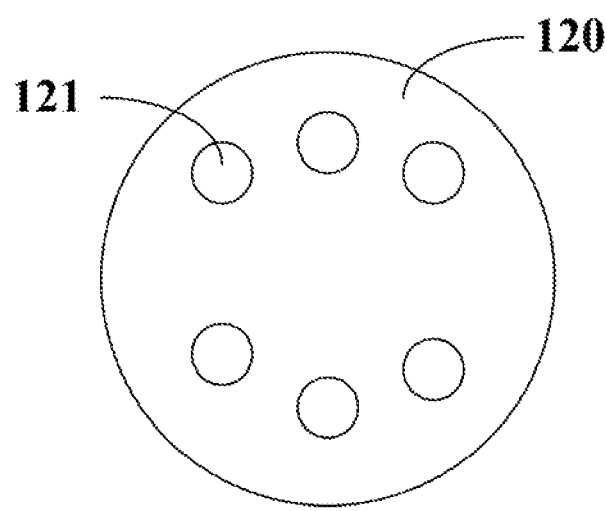
FIG. 5 is a detail diagram of the light source of FIG. 3.

FIG. 5 is a detail diagram of the light source 120 of FIG. 3. The light source 120 comprises six sub light sources 121. The six sub light sources 121 are a plurality of single color light emitting diodes (LEDs) which can be selectively turned on or off. For example, a FWHM wavelength of a first sub light source 121 is in 450-470 nanometers; a FWHM wavelength of a second sub light source 121 is in 512-538 nanometers; a FWHM wavelength of a third sub light source 121 is in 547-576 nanometers; a FWHM wavelength of a fourth sub light source 121 is in 579-591 nanometers; a FWHM wavelength of a fifth sub light source 121 is in 615-628 nanometers; and a FWHM wavelength of a sixth sub light source 121 is in 657-672 nanometers. Also, it is able to add other sub light source with different FWHM wavelength on different demands, whereas the FWHM wavelengths generated by the sub light sources 121 are not overlapped with each other. That is because the non-overlapped FWHM wavelengths can be used to more accurately detect the plurality of fluorescence labeled analytes which can react against specific wavelengths.

Because the sub light source 121 can be selectively turned on or off; in other words, it is able to only turn on the first to second sub light sources 121 or the third to fifth sub light sources 121, according to different needs, for the plurality of different fluorescence labeled analytes 110.

Figure 6:
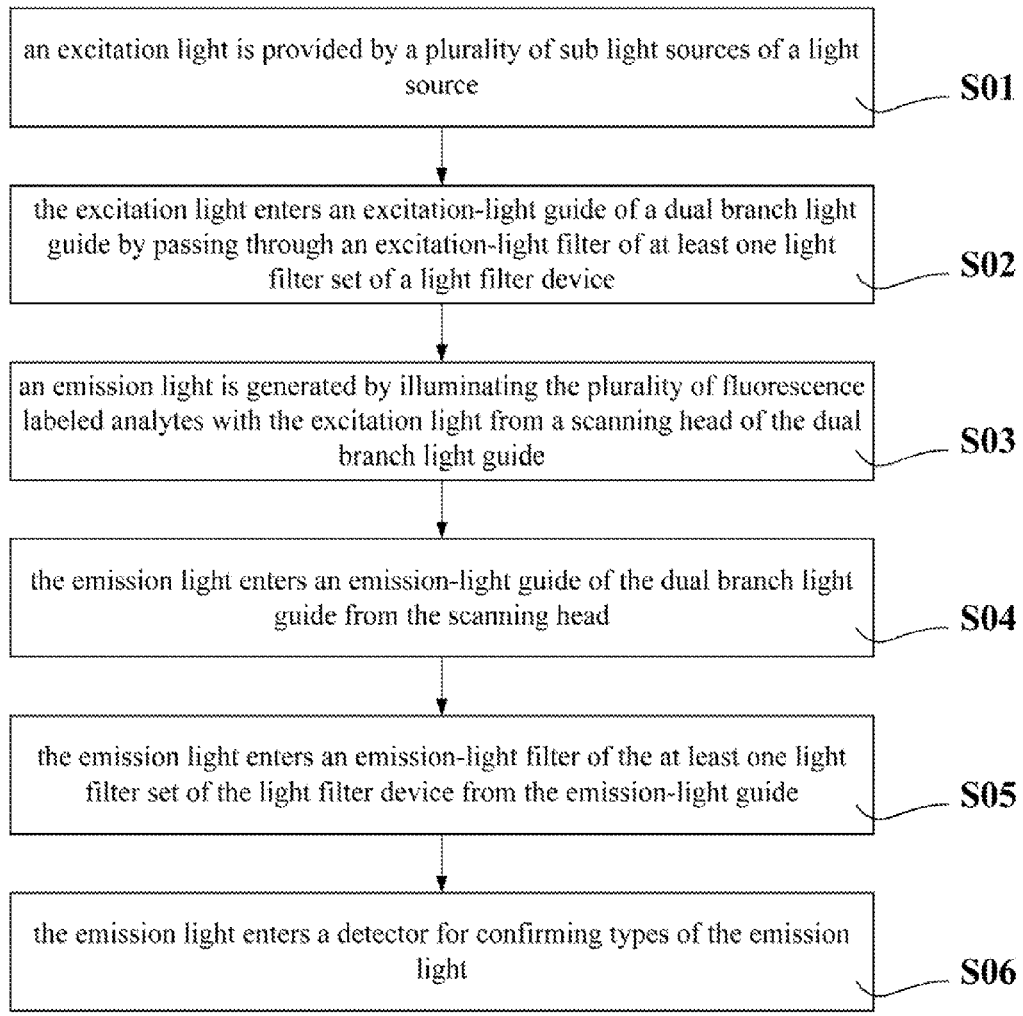
FIG. 6 is a flow diagram of a fluorescence detecting method according to the present invention.

FIG. 6 is a flow diagram of a fluorescence detecting method according to the present invention. As for the numeral of the elements used in the flow diagram, please refer to FIGS. 3-5. First, proceeding step S01, an excitation light 161 is respectively provided by a plurality of sub light sources 121 of a light source 120; next, proceeding step S02, the excitation light 161 enters an excitation-light guide tube 141 of a dual branch light guide tube 140 after passing through an excitation-light filter 1311 of at least one light filter set 131 of a light filter device 130; next, proceeding step S03, an emission light 162 is generated by illuminating the plurality of fluorescence labeled analytes 110 with the excitation light 161 from a scanning head 143 of the dual branch light guide tube 140; next, proceeding step S04, the emission light 162 from the scanning head 143 enters an emission-light guide tube 142 of the dual branch light guide tube 140; next, proceeding step S05, the emission light 162 from the emission-light guide tube 142 enters an emission-light filter 1312 of the at least one light filter set 131 of the light filter device 130; and next, proceeding step S06, the emission light 162 enters a detector 150 used for confirming types of the emission light 162.

Figure 7:
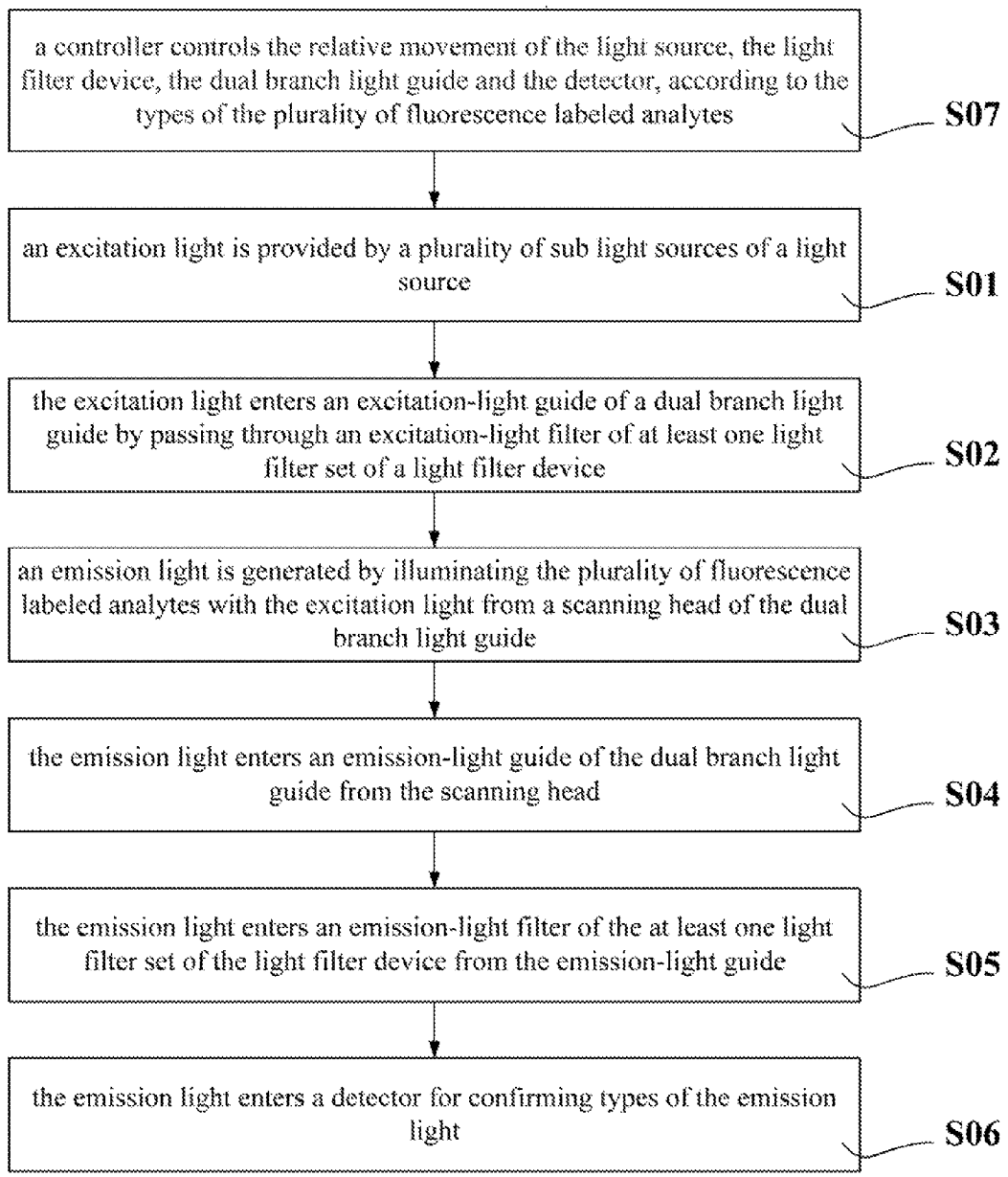
FIG. 7 is a flow diagram of a fluorescence detecting method according to a second preferred embodiment of the present invention.

FIG. 7 is a flow diagram of a fluorescence detecting method according to a second preferred embodiment of the present invention. A difference of the second preferred embodiment from the first preferred embodiment is that: the second preferred embodiment proceeds a step S07 before step S01. In step S07, a controller 170 controls relative movements among the light source 120, the light filter device 130, the dual branch light guide tube 140 and the detector 150, according to the types of the plurality of fluorescence labeled analytes 110.

As described above, although the present invention has been described with the preferred embodiments thereof, those skilled in the art will appreciate that various modifications, additions, and substitutions are possible without departing from the scope and the spirit of the invention. Accordingly, the scope of the present invention is intended to be defined only by reference to the claims.

What is claimed is:

1. A multi-channel fluorescence detecting system for detecting a plurality of fluorescence labeled analytes, comprising:
    a light source comprising a plurality of sub light sources for respectively providing an excitation light;
    a light filter device comprising at least one light filter set, each of which comprises an excitation-light filter and an emission-light filter, wherein the excitation-light filter is used to receive the excitation light;
    a dual branch light guide tube comprising an emission-light guide tube and an excitation-light guide tube, wherein the excitation-light guide tube is used to receive the excitation light passing through the excitation-light filter, the emission-light guide tube is used to receive the emission light which is generated, by the excitation light illuminating the plurality of fluorescence labeled analytes, with corresponding to the excitation light;
    a detector used to receive the emission light passing through the emission-light guide tube and the emission-light filter, for confirming types of the emission light; and
    a controller used for controlling relative movements among the light source, the light filter device, the dual branch light guide tube and the detector;
    wherein the controller controls the dual branch light guide tube to scan each of the plurality of fluorescence labeled analytes.

2. The multi-channel fluorescence detecting system according to claim 1, wherein the emission-light guide tube and the excitation-light guide tube are arranged, concentrically.

3. The multi-channel fluorescence detecting system according to claim 1, wherein the dual branch light guide tube further comprises a scanning head for making the excitation light to illuminate the plurality of fluorescence labeled analytes and for receiving the emission light.

4. The multi-channel fluorescence detecting system according to claim 1, wherein the light filter device further comprises a controlling device, which is used to cooperate with the excitation light and the emission light, for rotating the at least one light filter set.

5. The multi-channel fluorescence detecting system according to claim 1, wherein the plurality of sub light sources are a plurality of single color light emitting diodes (LEDs) which can be selectively turned on or off.

6. The multi-channel fluorescence detecting system according to claim 5, wherein the light source generates a plurality of lights with full width at half maximum (FWHM) wavelengths formed in a non-overlap manner.

7. A multi-channel fluorescence detecting method for detecting a plurality of fluorescence labeled analytes, comprising:
respectively providing an excitation light by a plurality of sub light sources of a light source;
the excitation light entering an excitation-light guide tube of a dual branch light guide tube after passing through an excitation-light filter of at least one light filter set of a light filter device;
generating an emission light by illuminating the plurality of fluorescence labeled analytes with the excitation light from a scanning head of the dual branch light guide tube;
the emission light, from the scanning head, entering an emission-light guide tube of the dual branch light guide tube;
the emission light, from the emission-light guide tube, entering an emission-light filter of the at least one light filter set of the light filter device;
the emission light entering a detector for confirming types of the emission light; and
a controller controlling relative movements among the light source, the light filter device, the dual branch light guide tube and the detector, according to the types of the plurality of fluorescence labeled analytes;
wherein the controller controls the dual branch light guide tube to scan each of the plurality of fluorescence labeled analytes.

8. The multi-channel fluorescence detecting method according to claim 7, wherein the dual branch light guide tube further comprises a scanning head for making the excitation light to illuminate the plurality of fluorescence labeled analytes and for receiving the emission light.

9. The multi-channel fluorescence detecting method according to claim 7, wherein the plurality of sub light sources are a plurality of single color light emitting diodes (LEDs) which can be selectively turned on or off.

10. The multi-channel fluorescence detecting method according to claim 9, wherein the light source generates a plurality of lights with full width at half maximum (FWHM) wavelengths formed in a non-overlap manner.

* * * * *